(12) United States Patent
McBroom

(10) Patent No.: US 7,736,452 B2
(45) Date of Patent: Jun. 15, 2010

(54) METHOD OF FORMING AND INDIRECT TESTING OF A BOND ON OR IN AN AIRCRAFT COMPONENT

(75) Inventor: Geoffrey P McBroom, Filton (GB)

(73) Assignee: Airbus Operations Limited, Bristol (GB)

( * ) Notice: Subject to any disclaimer, the term of this patent is extended or adjusted under 35 U.S.C. 154(b) by 385 days.

(21) Appl. No.: 10/499,364

(22) PCT Filed: Dec. 13, 2002

(86) PCT No.: PCT/GB02/05648

§ 371 (c)(1),
(2), (4) Date: Jun. 18, 2004

(87) PCT Pub. No.: WO03/055747

PCT Pub. Date: Jul. 10, 2003

(65) Prior Publication Data

US 2005/0006526 A1   Jan. 13, 2005

(30) Foreign Application Priority Data

Dec. 22, 2001   (GB) .................... 0130853.5

(51) Int. Cl.
*B32B 41/00*   (2006.01)
*B32B 37/12*   (2006.01)

(52) U.S. Cl. .................. 156/64; 156/94; 156/98; 156/344; 73/150 A

(58) Field of Classification Search .......... 156/64, 156/94, 98, 344, 378, 379, 584; 264/36.1, 264/36.18, 36.22; 374/4, 5; 228/103, 104; 73/1.09, 1.12, 150 A, 802, 847, 848
See application file for complete search history.

(56) References Cited

U.S. PATENT DOCUMENTS 2,681,877 A * 6/1954 Seymour .................. 156/240

(Continued)

FOREIGN PATENT DOCUMENTS

EP   0 401 991 A2   12/1990

(Continued)

OTHER PUBLICATIONS

Boeing News Features, "Fast Facts: Boeing 787", Boeing, downloaded from http://www.boeing.com/news/feature/sevenseries/787.html on Aug. 24, 2009.*

(Continued)

*Primary Examiner*—George R Koch, III
(74) *Attorney, Agent, or Firm*—Nixon & Vanderhye P.C.

(57) ABSTRACT

A method, in which a damaged site of a composite material structure, for example a wing skin on an aircraft, is repaired, includes the steps of repairing the damaged site with repair material, including adhesive, and at the same time bonding a test fixture, for example a button, at a test site next to the repair, by means of material that is the same as the repair material. The conditions to which the damaged site and the test site are subjected are substantially the same. After repair, the strength of the repair bond may be indirectly assessed by applying a torque to the test fixture, so as to assess the bond strength of the test fixture to the structure.

28 Claims, 3 Drawing Sheets

U.S. PATENT DOCUMENTS

| | | | | |
|---|---|---|---|---|
| 4,476,727 | A * | 10/1984 | Hawk et al. | 73/847 |
| 4,567,758 | A * | 2/1986 | Fisher et al. | 73/150 A |
| 5,190,611 | A | 3/1993 | Cologna et al. | |
| 5,442,156 | A | 8/1995 | Westerman et al. | |
| 5,709,469 | A | 1/1998 | White et al. | |
| 5,833,795 | A * | 11/1998 | Smith et al. | 156/272.4 |
| 6,149,749 | A * | 11/2000 | McBroom | 156/94 |
| 6,174,392 | B1 | 1/2001 | Reis | |
| 6,206,067 | B1 | 3/2001 | Kociemba et al. | |
| 6,341,544 | B1 * | 1/2002 | Falzone | 81/128 |
| 7,143,670 | B2 * | 12/2006 | Geary | 81/180.1 |
| 2001/0008161 | A1 * | 7/2001 | Kociemba et al. | 156/94 |

FOREIGN PATENT DOCUMENTS

EP 0 794 430 A2 9/1997

OTHER PUBLICATIONS

"U.S. Composite Repair Efforts Focus on Thermoplastic Materials"; Aviation Week and Space Technology, McGraw-Hill Inc., New York, US, vol. 132, No. 21, May 21, 1990, p. 110, XP000147984.

Dehm et al; "Fast, In-Situ Repair of Aircraft Panel Components"; Journal of Aircraft, American Institute of Aeronautics and Astronautics, New York, US, vol. 26, No. 5, May 1, 1989, pp. 476-481, XP000068955.

Hughes; "Canadians Develop Composite Techniques for CF-18 Battle Damage Repair Program"; Aviation Week and Space Technology, McGraw-Hill Inc., New York, US, vol. 132, No. 21, May 21, 1990, pp. 106, 107, 109, XP000147983.

ASTM D4541-85 (1985), "Standard Test Method for Pull-Off Strength of Coatings Using Portable Adhesion Testers" pp. 1-7.

* cited by examiner

METHOD OF FORMING AND INDIRECT TESTING OF A BOND ON OR IN AN AIRCRAFT COMPONENT

This application is the US national phase of international application PCT/GB02/05648 filed 13 Dec. 2002, which designated the US. PCT/GB02/05648 claims priority to GB Application No. 0130853.5 filed 22 Dec. 2001. The entire contents of these applications are incorporated herein by reference.

The present invention relates to a method of forming a bond on or in an aircraft component, for example, when repairing damage to an aircraft component or when manufacturing an aircraft component. The method relates in particular, but not exclusively, to repairing a damaged aircraft component formed from a laminated composite material.

In the aircraft industry there has been a reluctance to perform repair work to damaged safety-critical load-bearing structures of an aircraft, especially where the repair work includes forming a bond which must in use be able to withstand significant loading. It is believed that this reluctance results from the difficulties associated with demonstrating, without interfering with or affecting the bond, that the bond is able to sustain the loads necessary to facilitate safe operation.

The present invention seeks to provide a method of forming a bond on or in an aircraft component, wherein the confidence in the quality of the bond made may be improved.

According to a first aspect of the present invention there is provided a method of forming a bond comprising the following steps:

providing an aircraft component including a first site at which a bond is required, forming the bond with bonding material at the first site, bonding a test element at a second site of the aircraft component thereby forming a test bond, the second site being in the vicinity of the first site, the test element being so arranged that, after bonding the test element, the strength of the test bond may be assessed, wherein the test element is bonded to the aircraft component with the use of material that is the same as the bonding material, and the conditions to which the second site is subjected during the forming of the test bond are substantially the same as the conditions to which the first site is subjected during the forming of the bond, whereby after the forming of the bond at the first site, the strength of the bond so formed may be assessed, without needing to test the bond directly, by assessing the strength of the test bond.

The bond may be formed between the component and a further component, between the component and material used to repair damage, or between the component and any other object or material that is required to be bonded to the aircraft component. The method is of particular advantage where the bond is relied upon for safe operation of an aircraft, of which the aircraft component is a part, for example if the bond forms or is a part of a repair to a wing skin of an aircraft.

According to the method of the present invention, the strength of the bond at the first site may be assessed, without needing to test the bond directly, by assessing the strength of the test bond of the test element and thus there may be increased confidence in the quality of the bond formed at the first site. It will be understood that the assessment of the strength of the bond at the first site need not, and indeed preferably does not, assess the force required to cause failure of the test bond of the test element. On the contrary, the assessment preferably includes a step of applying a force to the test element of a magnitude great enough to provide confidence in the integrity of the test bond and therefore of the bond formed at the first site, whilst not applying a force significantly greater than necessary for that purpose. The test element advantageously does not serve any structural function other than as required by the present invention.

It will also be understood that the bonding conducted at the first site may be performed in a conventional manner using conventional materials. Thus, whilst the bond at the first site may be of a quality no better than that achievable with methods of the prior art, the method of the present invention provides a means of measuring indirectly the quality or strength of that bond.

The second site is advantageously directly adjacent to the first site. By having the first and second sites adjacent to each other it is easier to ensure that the two sites are subjected to the same conditions during performance of the method. It is known that, during subsequent operation, certain types of bond can deteriorate unacceptably rapidly in hot and/or wet conditions. During subsequent operation of the component, the first and second sites, by being adjacent, are also more likely to be subjected to identical conditions, and thus an assessment as to whether those conditions have caused the bond at the first site to deteriorate unacceptably can be made by testing the test bond. Thus, it is preferable for the test element to be positioned as close as possible to the bond at the first site. Advantageously, however the test element is not located at a position that is so close to the bond at the first site as to interfere with the bond or the forming of the bond. Preferably, therefore, the second site is close to, but excludes, the first site.

The steps of forming the bond at the first site and of bonding a test element may incorporate the use of a bonding material, for example an adhesive, that is heat cured. The bonding material may be in the form of a film adhesive, for example, an epoxy adhesive held by a fibrous thin film. In a case where a heat cured bonding material is used, the bonding of the test element is preferably performed in such a way as to produce a test bond having a predetermined contact area. A barrier may, for example, be provided to limit the flow of the bonding material during the curing of the test bond. Forming a test bond having a predetermined area may aid any calculations that may be required to assess the strength of the test bond. The bonding of the test element preferably includes the steps of positioning a skirt around the bonding material used to bond the test element to the aircraft component, then heat curing the bonding material, and then removing the skirt. The use of such a skirt may facilitate the formation of a well-defined edge to the test bond between the test element and the aircraft component. The method may include steps of simultaneously curing the bond material at the first site and at the second site, for example, by heat curing with the same heater blanket under vacuum. Thus the heating cycle to which the bond at the first site is exposed is advantageously the same heating cycle to which the test bond of the test element is exposed.

The forming of the bond at the first site may include a step of preparing the surface of the component. In such cases, the second site is preferably also prepared in a way that ensures that the properties and characteristics of the second site insofar as they might affect the quality of the test bond are substantially identical to the corresponding properties and characteristics of the first site. Where the first site is prepared prior to forming the bond, the method may for example include a step of preparing the surface of the component at the second site in a substantially identical manner. Such preparations may include abrading the surface and/or cleaning the surface, for example by swabbing with a solvent.

The conditions to which the second site is subjected during the method may, as far as is practically possible, be substantially the same as the conditions to which the first site is subjected. The method, insofar as it is performed by a person, is preferably performed by the same person.

More than one type of material may be used when forming the bond and test bond. There may be a cushion between the component and the test element, the cushion optionally being integrally formed with the test element. The respective surfaces of the test element and of the aircraft component that are to be bonded together might not necessarily be the same shape. For example, the surface of the test element may be planar, whereas the surface of the aircraft component may be non-planar. Providing a cushion between the two surfaces may aid the formation of a suitable test bond.

The test element is preferably relatively small in size, and may, for example, have a maximum dimension that is less than 50 mm, and more preferably less than 30 mm.

The aircraft component may be formed of a laminated composite material structure. In such a case, the steps of forming a bond and of bonding a test element preferably incorporate the use of at least one ply of laminate composite material. Said at least one ply of laminate composite material may form the cushion as described above. Said at least one ply of laminate composite material may be in the form of woven glass fibre and/or carbon fibre cloth pre-impregnated with epoxy resin.

Alternatively, the aircraft component may be formed of a metal. In such a case, the steps of forming a bond and of bonding a test element may involve metal bonding techniques such as welding.

Preferably, a composite material forms at least the majority of the portion of the test element that is bonded to the aircraft component. Preferably, the majority of the portion (or the surface) of the test element that is bonded to the aircraft component is formed of a material that is of the same type of material as that of the material, or of the portion of the object, that is bonded with the bond at the first site to the aircraft component. For example, if the bond at the first site is part of a composite material repair, the surface of the test element bonded with the test bond is mainly, or preferably completely, of the same composite material. The test element may include a woven fibre reinforced composite material body. The test element may additionally have a structure that includes metal. For example, the test element could be in the form of a metal support structure around which there is bonded a composite material body. The metal support structure may for example provide a portion that enables a force, for example a torque, to be applied to the test element. The composite body may for example provide the surface that is bonded to the aircraft component. Such features are especially advantageous in the case where the aircraft component is a composite material structure.

The test element is advantageously arranged so that it is possible to assess the shear strength of the test bond in a controlled manner. The test element advantageously has a portion so shaped that it is able to co-operate with a corresponding portion of a tool for applying a torque. The portion of the test element is preferably in the form of at least one recess so that the tool is in the form of a key. Other configurations are of course possible. For example, the test element may have a head in the shape of a nut that may co-operate with a conventional spanner, for example a torque wrench.

The method advantageously includes performing a further step, after forming the bond, of applying a force to the test element to assess indirectly the strength of the bond. Such a step is preferably applied immediately after the bond has been formed and the formation of the test bond has been completely formed (allowing for any rest, cooling, curing, or setting time that may in the circumstances be required). This further step is also preferably performed periodically during operational use of the aircraft component so that the integrity of the bond can be monitored throughout the lifetime of the component.

The force applied to the test element, when indirectly assessing the strength of the bond at the first site, is preferably selected to correspond to a force that is equal to or greater than the minimum load that the bond at the first site must be able to withstand to be judged as being sufficiently strong for safe operational use of the component. Preferably, the force applied is selected to be significantly greater than the force corresponding to that minimum load, but significantly less than the force required to cause failure of the test bond. For example, the bond material may be chosen to have properties such that the bond when formed in ideal conditions can withstand forces at least 6 times greater than the maximum load that would be expected during normal operation. It may be possible in exceptional circumstances for the loads sustained during operation to be up to 2.5 times those loads experienced during normal operation. The minimum load (determining the force to be applied) may in this case therefore be about 3 times the maximum load sustained during normal operation, that is significantly higher than loads normally experienced, higher than the maximum load expected in the most exceptional of cases and yet only half the theoretical ultimate strength of the bond. The force is preferably applied once only during each assessment. The force is preferably applied for a period of between 0.1 and 10 seconds. In tests carried out the force has been applied for one or two seconds. The force is preferably applied in the form of an applied torque.

The bond may be formed at the first site as part of a step of repairing a damaged portion at the first site of the aircraft component. Such damage may be caused by impact for example.

Thus the present invention provides, according to a second aspect, a method of repairing a damaged aircraft component, the method comprising the following steps:

providing an aircraft component having a damaged portion at a first site, repairing the damaged portion with repair material, fixing a test element at a second site of the aircraft component, the second site being in the vicinity of the first site, the test element being so arranged that, after fixing, the bond strength of the fixing of the test element may be assessed, wherein the test element is fixed to the aircraft component with the use of material that is the same as the repair material, and the conditions to which the second site is subjected during the step of fixing are substantially the same as conditions to which the first site is subjected during the step of repairing, whereby after repair of the damaged portion, the strength of the repair bond may be assessed, without needing to test the repair bond directly, by assessing the bond strength of the fixing of the test element.

According to a third aspect of the present invention there is provided a method of repairing a damaged composite material structure, the structure forming an aircraft component or a part thereof, the method comprising the following steps:

providing a composite material structure having a damaged portion at a first site, repairing the damaged portion with repair material, fixing a test element at a second site of the composite material structure, the second site being in the vicinity of the first site, the test element being so arranged that, after fixing, the bond strength of the fixing of the test element may be assessed, wherein the test element is fixed to the composite material structure with the use of material that is the same as the repair material, and the conditions to which the second site is subjected during the step of fixing are substantially the same as conditions to which the first site is subjected during the step of repairing, whereby after repair of the damaged portion, the bond strength of the repair may be assessed, without needing to test the repair bond directly, by assessing the bond strength of the fixing of the test element.

The method of the invention also has application where the bond is formed at the first site as part of a step of manufacturing an aircraft component. Thus the present invention provides, according to a fourth aspect, a method of manufacturing an aircraft component including a step of bonding two objects to one another, wherein the step of bonding is performed in accordance with the method of the first aspect of the invention as defined above. The objects may of course be different in nature, type, shape, or other characteristics.

According to a fifth aspect of the invention there is provided an aircraft component produced in accordance with a method of any of the first to fourth aspects of the present invention.

According to a sixth aspect of the invention there is provided an aircraft including an aircraft component according to the fifth aspect of the present invention. The aircraft may for example have been damaged and repaired in accordance with the present invention The present invention yet further provides according to a seventh aspect a kit including bonding material for forming a bond and a test element, the kit advantageously being suitable for forming a bond according to the method of any of the first to fourth aspects of the present invention. The kit of parts may for example form a repair kit.

Various embodiments of the present invention will now be described by way of example with reference to the accompanying drawings, of which:

The first embodiment of the invention relates to a method of repairing a damaged section of a component of an aircraft, wherein the component is in the form of a laminated aircraft component. The damaged section of the component is repaired and at the same time a test button is bonded to the component in a position adjacent to the damaged section. The fixing of the test button to the component is conducted in exactly the same manner, insofar as that is possible, and at the same time as the repairing of the damaged section.

The damaged section is prepared for repair. The preparation of the damaged section includes machining the section to produce a low gradient (1 in 20 to 1 in 30) slope, then abrading with 120 grade wet & dry paper and treating the surface with a solvent, such as acetone. Machining the section to form the slope is a standard technique known in the art and the repair when completed is commonly referred to as a scarf repair. Such preparations (except the machining) are also carried out in respect of the region of the component where the test button is to be fixed so that the surface of the prepared (previously damaged) section matches as closely as possible the surface onto which the button is to be fixed. Also, the same materials are used to bond the button to the component as are used in the repair work. The repair materials used in this instance comprise a layer of 120° C. cure woven carbon fibre cloth preimpregnated with epoxy resin, and a layer of film adhesive (a sheet of epoxy adhesive, having good wetting out properties, carried on a very thin fibrous substrate). The bonding materials used in relation to the button and the repair are cured simultaneously with the same vacuum bag and heat blanket, so that the curing is effected at the same time and under the same conditions. For example, the bonding materials are subjected to the same vacuum for the same length of time, and are subjected to the same heat cycle during the cure. In this case, the repair and button were simultaneously bonded using a 90 minute cure at a constant temperature of 120° C. under vacuum. The work is carried out by the same operator. Thus the mechanical properties of the bonding beneath the button and beneath the repair should be very closely matched.

Figure 1:
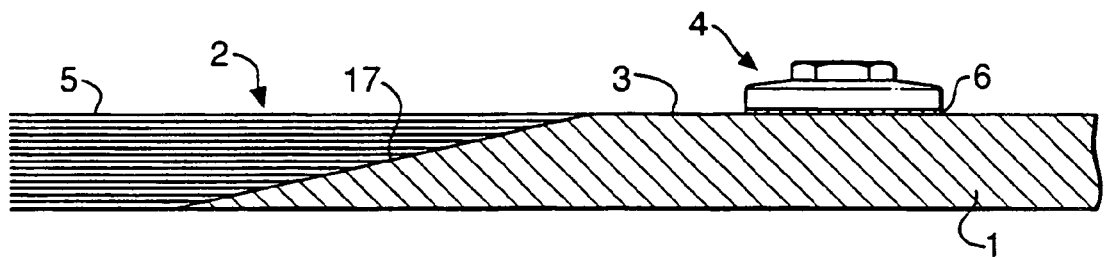
FIG. 1 shows a button and a component repaired in accordance with a first embodiment of the invention.
Figure 3:
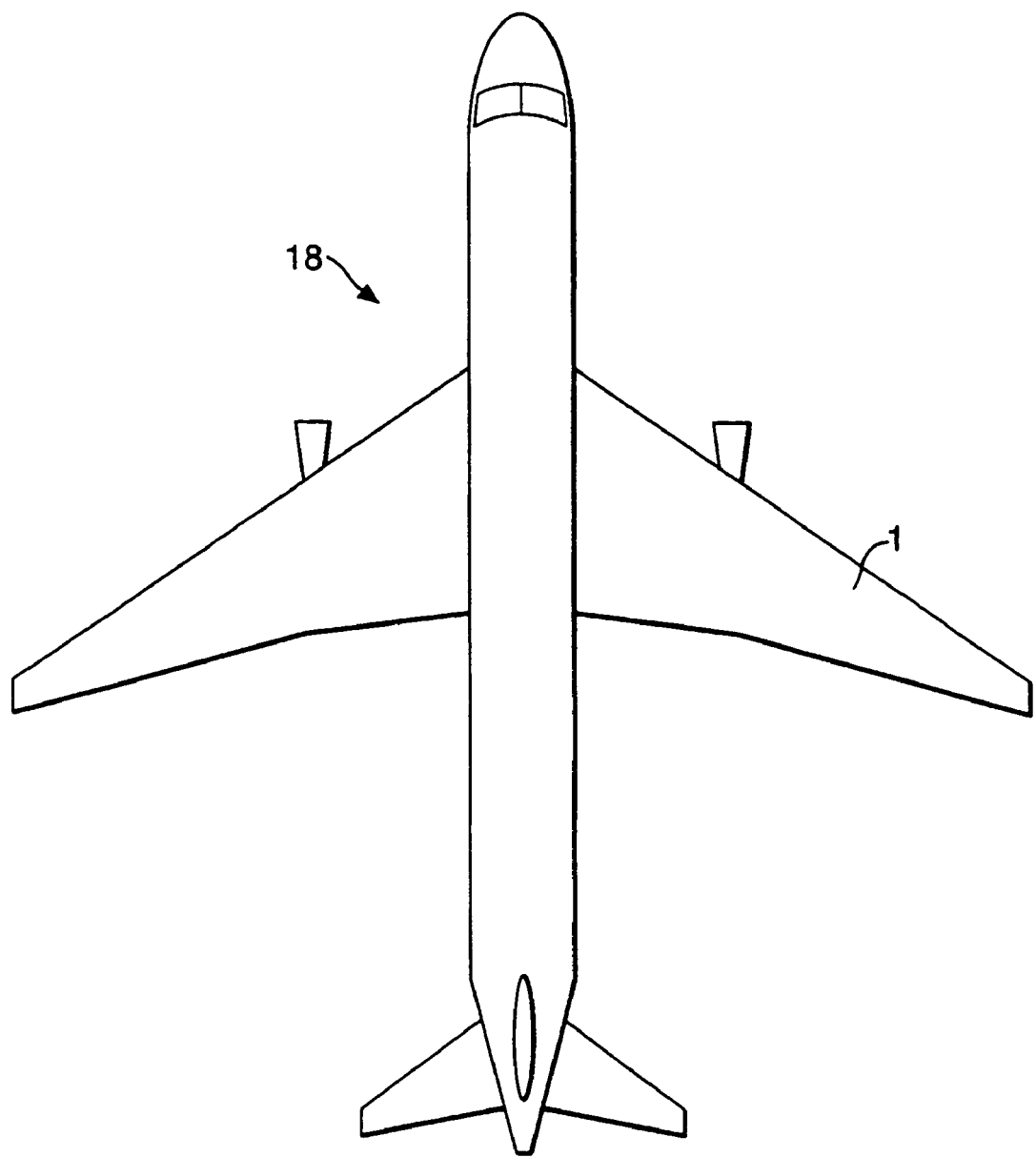
FIG. 3 shows an aircraft including the component shown in FIG. 1.

FIG. 1 shows a section of a wing skin 1 of an aircraft 18 (shown in FIG. 3) after it has been repaired in accordance with the first embodiment of the present invention. The skin 1 includes a repaired section 2 and a test section 3 including a test button 4 bonded to the wing skin 1. The skin 1 is formed of a laminated aircraft component, the composite material being a 16 ply, 4 mm thick quasi-isotropic lay-up. (Of course the lay-up and orientation of the plies is chosen to match that of the region being repaired.) The material 5 used to repair the damaged section is the same as the material 6 used to bond the button 4 to the skin 1. The repaired section includes a machined slope 17 having a shallow gradient of 1 in 20 (the gradient is not shown to scale in FIG. 1).

Figure 2:
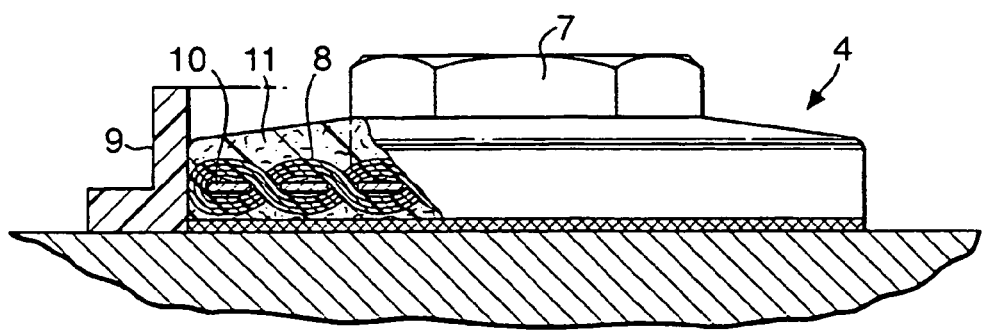
FIG. 2 shows the button shown in FIG. 1 in more detail.

FIG. 2, showing the button in greater detail, includes a cut-away section showing the internal structure of the button 4. The button 4 has a basic steel structure that forms a hexagonal head 7 and a plate 10 to which the head 7 is attached, the plate 10 having a ring of holes formed therein. The head 7 is about an inch in diameter (25 mm). A thick tow of dry glass fibres 8 is woven through the holes in the plate 10. The plate 10 of the steel structure and the glass fibres 8 are encased by a composite material 11 formed from a slurry of epoxy resin loaded with chopped strands of glass fibre, the slurry having been cured at 130° C. The head 7 of the button 4 is thus exposed. The button 4 also includes a removable plastic surround 9 (only part of which is shown in FIG. 2) that is used, during the fixing of the button to the skin 1, to produce a well defined edge to the bond-line between the button 4 and the skin 1. After curing of the bond between the button 4 and the skin 1, the plastic surround 9 is removed.

The strength of the button 4 may then be tested by applying a given shear stress. The shear stress applied is chosen to exceed the shear stress that the repaired damaged section 2 must be able to withstand during normal operation plus a margin of tolerance (say 50%) whilst not being so great as to exceed the ultimate shear strength of the button 4. A torque is applied to the button 4 via the hexagonal head 7 using a conventional torque wrench. The torque applied is equal to (or greater than) a torque Tmin, where $T_{min} = \frac{1}{2} Pi.r^3 S_{safe}$, where r is the average radius of the button and $S_{safe}$ is the minimum shear stress that the repaired section must be able to withstand for safe operation of the component. For example, if a component must be able to withstand shear stresses of the order of 10 MPa during normal operation, the test may require that the button be subjected to a shear stress of the order of 15 MPa to enable the repair to be determined as satisfactory. The torque applied would, for a button having a radius of 0.0125 m (12.5 mm), therefore need to be 46 Nm. If the bond 6 between the button 4 and the skin 1 can withstand such an applied torque then it is assumed that the repair has been successfully made. The integrity of the bond 6 between the button 4 and the skin 1 may thereafter be tested from time to time to assess whether the repaired section 2 is still of a satisfactory standard.

Tests have shown that the structure of the button 4 can withstand torques up to 80 Nm, which is easily in excess of the torques required to be applied during normal testing.

Figure 4A:
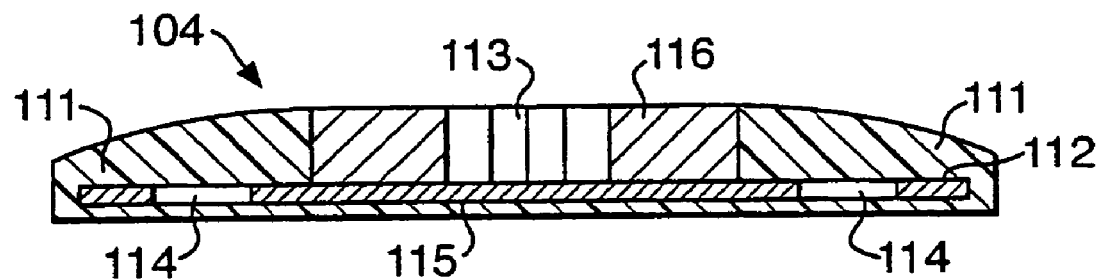
FIGS. 4a and 4b show a button for use in a second embodiment of the invention.
Figure 4B:
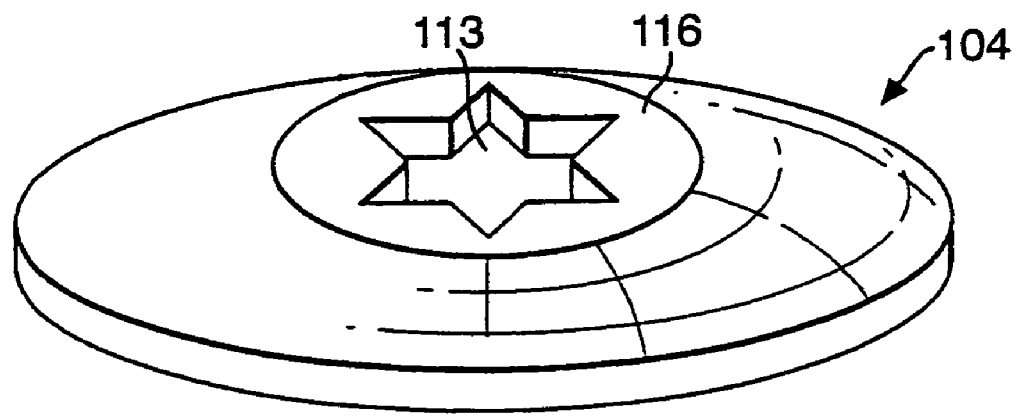

FIGS. 4a and 4b show a button 104 in accordance with a second embodiment of the invention. FIG. 4a shows the button 104 in cross-section and FIG. 4b is a perspective view of the button 104. The button 104 is in the general form of a flat disc having a diameter of about 20 mm. The button 104 in this case comprises a glass-fibre reinforced polymer resin body 111, which surrounds a steel structure 115. The steel structure 115 has a disc shaped base 112 and a head 116 connected to the base 112. The head 116 has a recess 113 having a cross-section in the shape of a 6 pointed star. The recess 113 acts as a socket into which a suitably shaped key (not shown) may be inserted in order to apply a torque to the button 104. The resin body 111 does not extend into or over the recess 113 of the head 116 or the upper surface of the head 116 (in the orientation shown in FIGS. 4a and 4b). The disc shaped base 112 has a ring of holes 114 around its periphery to aid the bonding of the metal structure 115 to the resin body 111. The method of the second embodiment is otherwise identical to the method of the first embodiment described above with reference to FIGS. 1 to 3.

Of course various modifications can be made to the above described embodiments without departing from the scope of the invention. For example, the button of the first embodiment need not be reinforced with the woven glass fibres 8. The invention is not of course limited to making repairs and similar methods to the embodiments described above may be used when manufacturing aircraft components.

The invention claimed is:

1. A method of non-destructively testing a bond comprising the following steps:
   providing an aircraft component including a first site at which said bond is required, wherein the aircraft component is a laminated composite material structure,
   forming the bond with bonding material at the first site,
   bonding a test element at a second site of the aircraft component thereby forming a test bond, the second site being in the vicinity of the first site, the test element being so arranged that, after bonding the test element, the strength of the test bond may be assessed, wherein the test element is bonded to the aircraft component with the use of material that is the same as the bonding material, and the conditions to which the second site is subjected during the forming of the test bond are substantially the same as the conditions during the forming of the first site bond, and
   after the forming of the first site bond, non-destructively assessing the strength of the first site bond by measuring the strength of the test bond by applying a force to the test element, and the steps of forming a bond and of bonding a test element incorporate the use of at least one ply of laminate composite material.

2. A method according to claim 1, wherein the second site is directly adjacent to the first site.

3. A method according to claim 1, wherein the steps of forming the bond and of bonding a test element incorporate the use of bonding material that is heat cured.

4. A method according to claim 1, wherein the step of bonding the test element is performed in such a way as to produce a test bond having a predetermined contact area.

5. A method according to claim 3, wherein the step of bonding the test element includes positioning an open ended surround around the bonding material used to bond the test element to the aircraft component, then heat curing the bonding material, and then removing the surround.

6. A method according to claim 1, wherein the test element has a portion so shaped that it is able to co-operate with a corresponding portion of a tool for applying a torque and said step of assessing the strength of the test bond includes applying a torque to said test bond.

7. A method according to claim 6, wherein said so shaped portion comprises a head in the shape of a nut and the step of measuring the strength of the test bond includes applying a torque wrench to the head in the shape of a nut.

8. A method according to claim 6, wherein said so shaped portion comprises a socket and the step of measuring the strength of the test bond includes applying a torque wrench the socket.

9. A method according to claim 8, wherein said socket is a six pointed star and the step of measuring the strength of the test bond includes applying a torque wrench to the star.

10. A method according to claim 6, wherein said so shaped portion of said test element is metal and another portion of said test element which is bonded to said second site is a composite material.

11. A method according to claim 10, wherein said test element comprises a metal support structure which is at least partially surrounded by a composite material body.

12. A method according to claim 1, wherein the first site bond is formed at the first site as part of a step of repairing a damaged portion at the first site of the aircraft component.

13. A method according to claim 1, wherein the first site bond is formed at the first site as part of a step of manufacturing an aircraft component.

14. A method of non-destructively testing a composite bond on an aircraft structure, said method comprising the steps of:
   forming the composite bond with bonding material at a first site on said structure;
   bonding a test element to said structure at a second site on said structure using materials and bonding processes that are similar to the forming step, the second site being in the vicinity of the first site, wherein the test element has a portion so shaped that it is able to co-operate with a corresponding portion of tool for applying a torque; and
   after the forming of the first site bond and bonding said test element at said second site, non-destructively assessing the strength of the first site bond by measuring the strength of the test bond at said second site by applying torque to the test element.

15. A method according to claim 14, wherein the second site is directly adjacent to the first site.

16. A method according to claim 14, wherein the steps of forming the first site bond and of bonding a test element incorporate the use of bonding material that is heat cured and the step of bonding the test element includes positioning an open ended surround around the bonding material used to bond the test element to the aircraft structure, then heat curing the bonding material, and then removing the surround.

17. A method according to claim 14, wherein the aircraft structure is a laminated composite material structure and the steps of forming a first site bond and of bonding a test element incorporate the use of at least one ply of laminate composite material.

18. A method according to claim 14, wherein the first site bond is formed as part of a step of repairing a damaged portion at the first site of the aircraft structure.

19. A method according to claim 14, wherein the first site bond is formed as part of a step of manufacturing an aircraft structure.

20. A method according to claim 14, wherein said so shaped portion comprises a head in the shape of a nut and the step of measuring the strength of the test bond includes applying a torque wrench to the head in the shape of a nut.

21. A method according to claim 14, wherein said so shaped portion comprises a socket and the step of measuring the strength of the test bond includes applying a torque wrench to the socket.

22. A method according to claim 21, wherein said socket is a six pointed star and the step of measuring the strength of the test bond includes applying a torque wrench to the star.

23. A method according to claim 14, wherein said so shaped portion of said test element is metal and another portion of said test element which is bonded to said second site is a composite material.

24. A method according to claim 23, wherein said test element comprises a metal support structure which is at least partially surrounded by a composite material body.

25. A method according to claim 14, wherein said torque applied to said test element is greater than a minimum load that the composite bond at the first site must withstand.

26. A method according to claim 25, wherein said torque is applied to said test element only once.

27. A method according to claim 26, wherein said torque is applied to said test element for a duration of between 0.1 and 10 seconds.

28. A method according to claim 27, wherein said torque is applied to said test element for a duration of between 1 and 2 seconds.

\* \* \* \* \*